US006860623B2

(12) United States Patent
Liu

(10) Patent No.: US 6,860,623 B2
(45) Date of Patent: Mar. 1, 2005

(54) LAMP APPARATUS FOR LIGHTING AND HEATING

(76) Inventor: Yu-Peng Liu, 8F, No. 20, Alley 101, Lane 629, Sec. 1, Nei Hu Road, Taipei (TW)

( * ) Notice: Subject to any disclaimer, the term of this patent is extended or adjusted under 35 U.S.C. 154(b) by 0 days.

(21) Appl. No.: 10/437,302

(22) Filed: May 14, 2003

(65) Prior Publication Data

US 2004/0228126 A1 Nov. 18, 2004

(51) Int. Cl.[7] .............................................. F21V 21/00
(52) U.S. Cl. .......................... 362/392; 362/253; 362/92; 362/806
(58) Field of Search .................................. 362/412, 401, 362/92, 101, 398, 397, 392, 806, 810, 253

(56) References Cited

U.S. PATENT DOCUMENTS 5,197,741 A * 3/1993 Wu .............................. 273/237

* cited by examiner

Primary Examiner—Sandra O'Shea
Assistant Examiner—Ali Alavi
(74) Attorney, Agent, or Firm—Rosenberg, Klein & Lee

(57) ABSTRACT

The present invention relates to a lamp apparatus, which includes a lamp, a holder, and a connector. The lamp is received in the holder. The characteristic of the present invention is to provide a weight piece being received in the connector. The holder with the lamp is also connected within the connector above the weight piece (4) so the lamp apparatus can be positioned stably at any desire place.

1 Claim, 4 Drawing Sheets

LAMP APPARATUS FOR LIGHTING AND HEATING

BACKGROUND OF THE INVENTION

The present invention relates to a lamp apparatus for lighting and heating, which has a stable structure to be positioned at any desire place.

In some situation, a lamp apparatus for lighting and heating is provided to obtain a certain purpose. For example, a lamp apparatus is placed under a disk containing aromatherapy oil therein. The oil can be vaporized by the heat of the lamp apparatus for perfuming. At the same time, the lighting of the lamp apparatus promotes the decorative effect. But the conventional lamp apparatus can not be positioned stably since the lamp holder and the connector are usually made of plastic. If the conventional lamp apparatus is fallen, dangerous accident, such as a fire, could happen because of the heat of the lamp.

Accordingly, the present invention is to provide a lamp apparatus for lighting and heating, which can prevent from the drawback of the conventional structure.

BRIEF DESCRIPTION OF THE DRAWINGS

The following drawings indicate the character and improvement of the present invention.

DETAILED DESCRIPTION OF THE INVENTION

Figure 1:
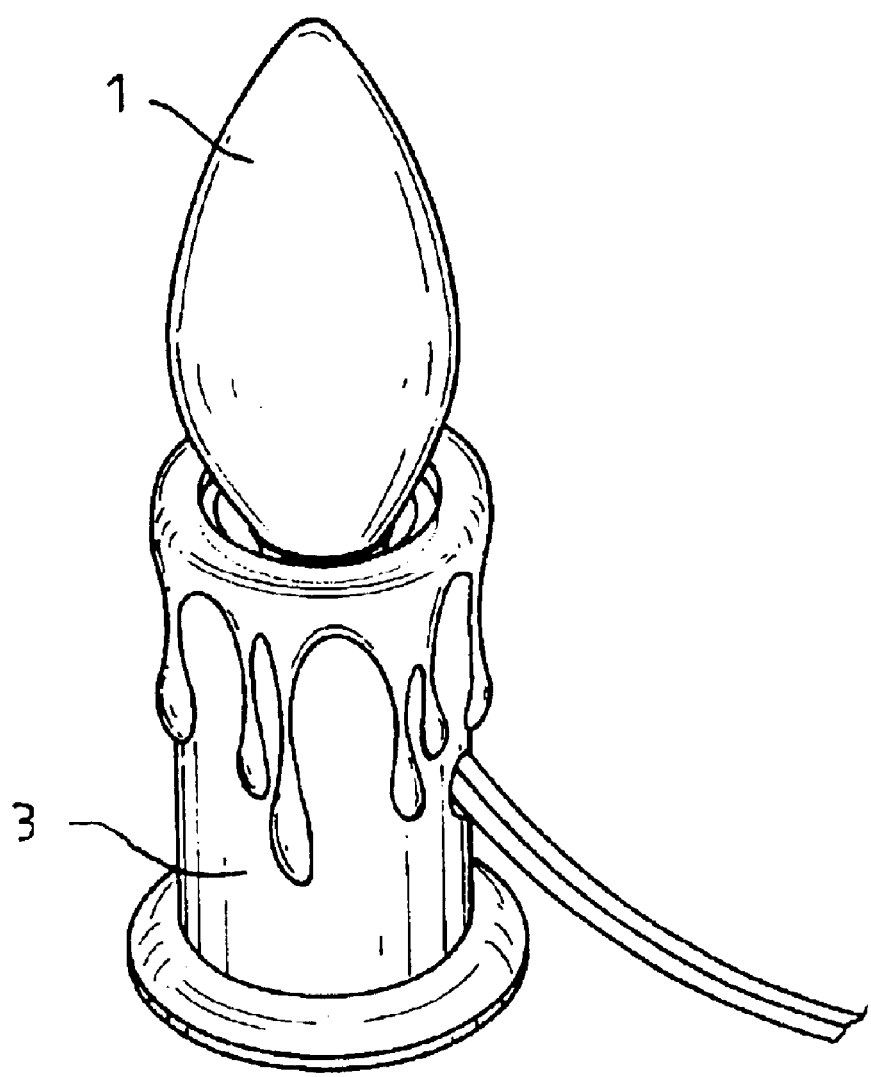
FIG. 1 shows a perspective view of a lamp apparatus according to the present invention.
Figure 2:
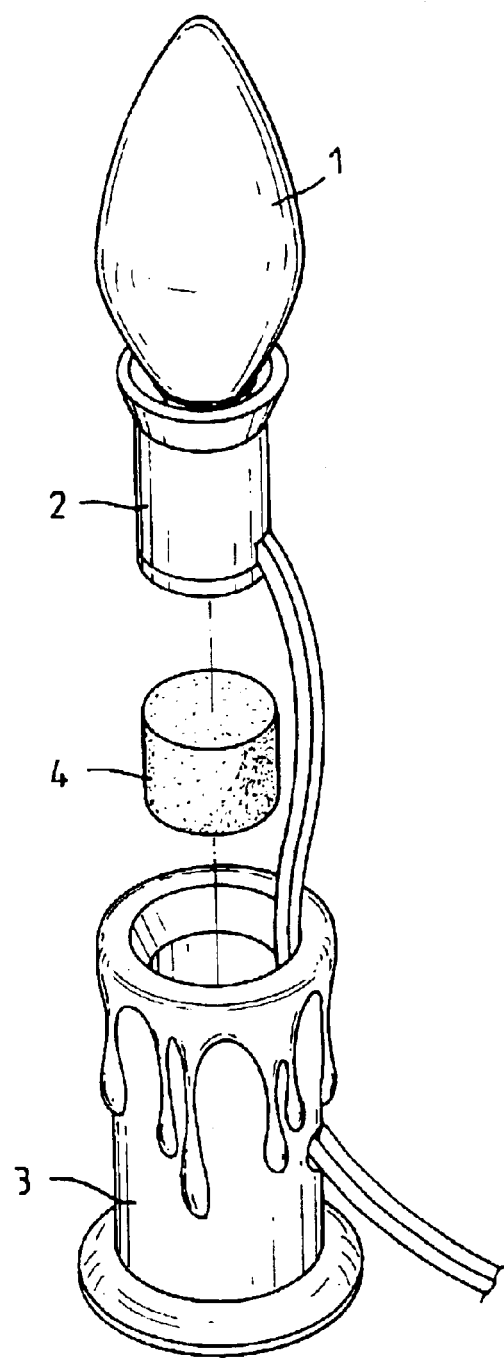
FIG. 2 shows an exploded perspective view of FIG. 1.

Referring firstly to FIGS. 1 and 2, the present invention relates to an improvement of a lamp apparatus for lighting and heating, which includes a lamp (1), a holder (2), and a connector (3). The lamp (1) is received in the holder (2). The characteristic of the present invention is to provide a weight piece (4) being received in the connector (3). The holder (2) with the lamp (1) is also connected within the connector (3) above the weight piece (4). Because the weight piece (4) is at lower position in the connector (3), the lamp apparatus can be then positioned stably while the center of the gravity has been moved downward. Hence, the lamp apparatus according to the present invention can prevent from being fallen of the prior one.

Figure 3:
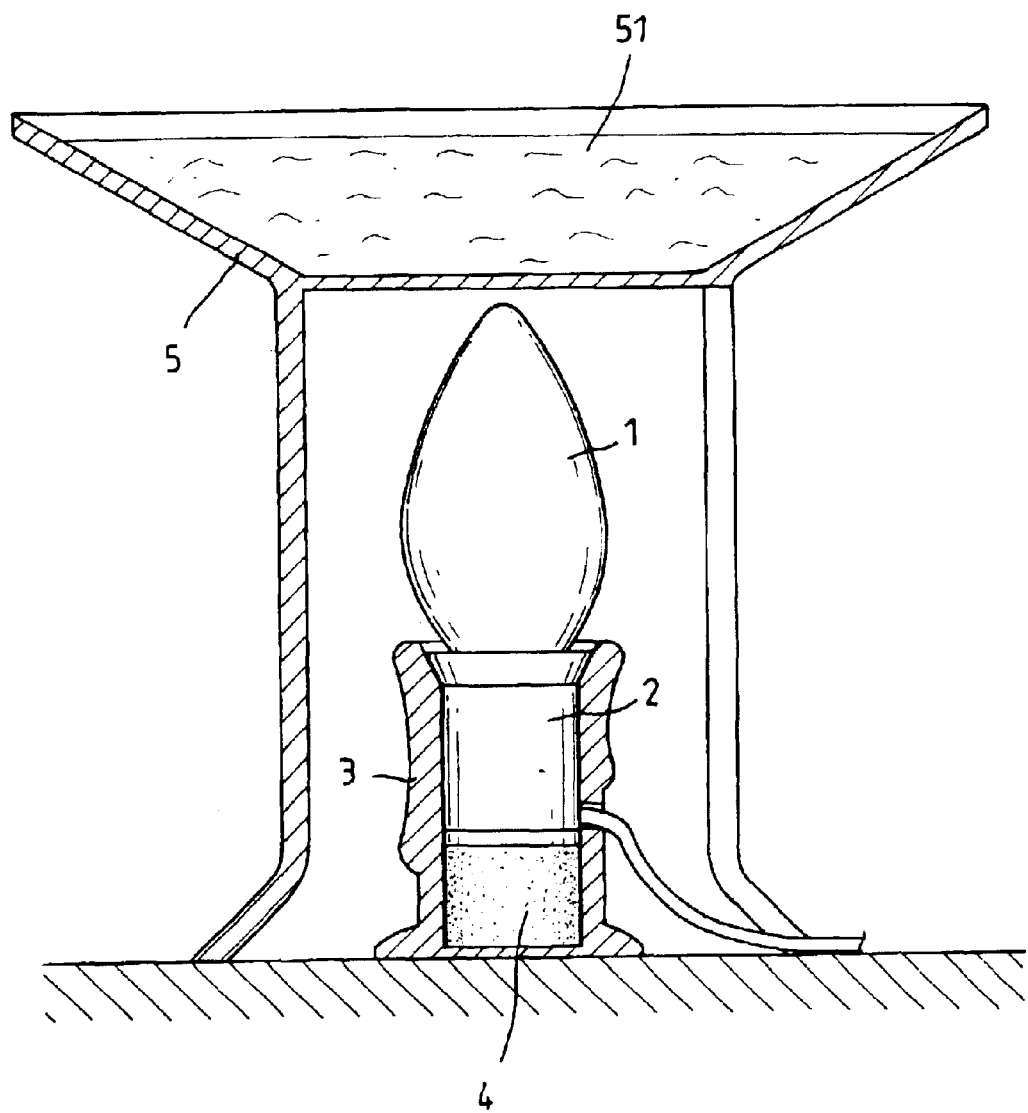
FIG. 3 is a cross-sectional plan view showing an application of the present invention.
Figure 4:
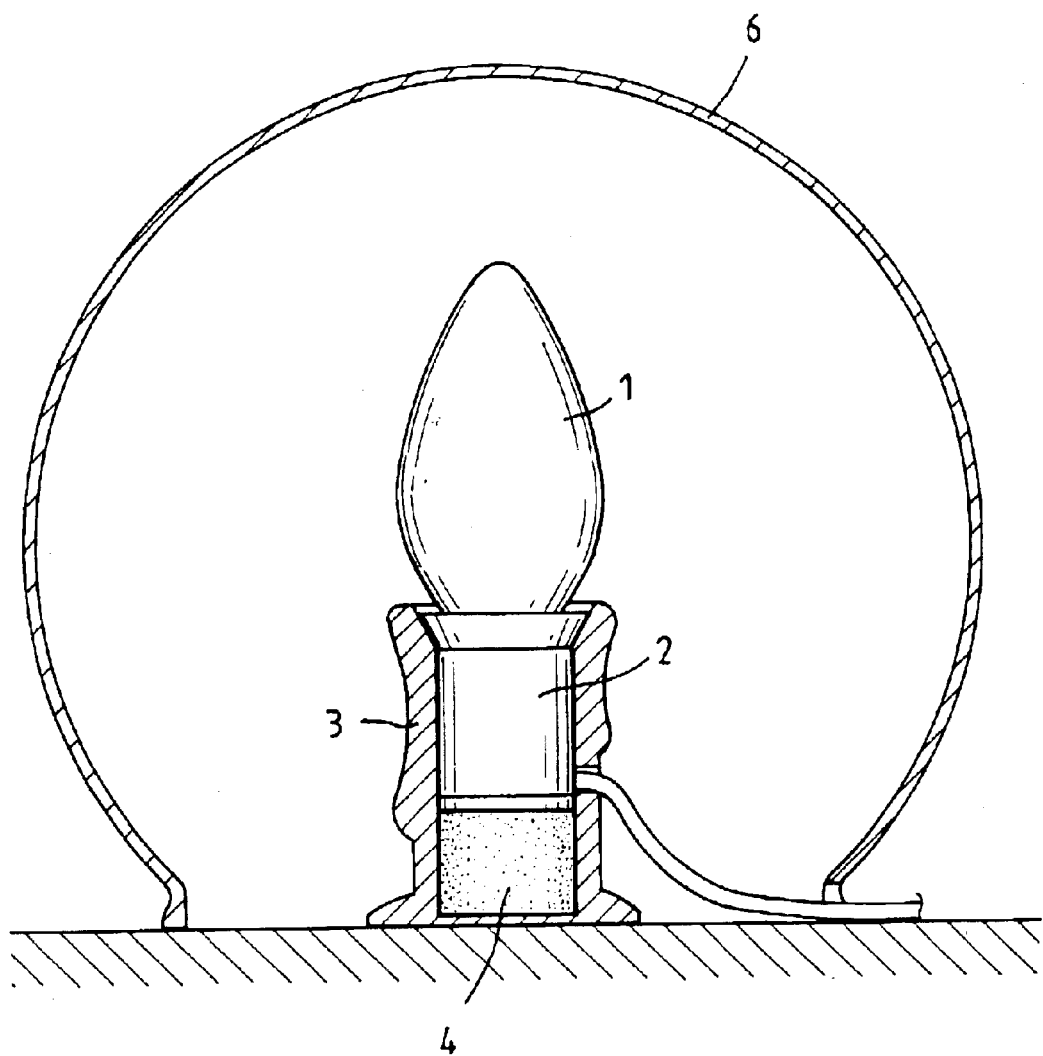
FIG. 4 is a cross-sectional plan view showing another application of the present invention.

In use, as shown in FIG. 3, the lamp apparatus of this invention can be placed under a disk (5) containing with aromatherapy oil therein. By the heat of the lamp (1), the oil can be vaporized and it can perfume all around. The lighting of the lamp can also increase the decorative effect. As shown in FIG. 4, it shows another embodiment of the present invention, wherein the lamp apparatus is covered by a decorative cover (6) and the lighting of the lamp can display the special decorative effect through the cover (6). At this moment, the lamp apparatus can be stably positioned always. Accordingly, the present invention obtains utility for use and should be allowed for patent.

What is claimed is:

1. A combined lighting and heating apparatus comprising:
   (a) a free standing connector member having an upper opening and a bore extending axially therefrom;
   (b) a lamp assembly supported by said connector member for display, said lamp assembly including:
      a lamp; and,
      a holder coupled to said lamp for supporting and energizing illumination of said lamp, said holder being inserted in said upper opening of said connector member to maintain said lamp extended from said connector member; and,
   (c) a weight piece insert captured by said lamp assembly at a bottom portion of said connector member bore.

* * * * *